(12) United States Patent
Langley et al.

(10) Patent No.: US 10,188,800 B2
(45) Date of Patent: Jan. 29, 2019

(54) DRIVE ASSEMBLY FOR A DRUG DELIVERY DEVICE AND DRUG DELIVERY DEVICE

(75) Inventors: Christopher Langley, Leamington Spa (GB); Christopher Jones, Tewkesbury (GB); Paul Draper, Evesham (GB)

(73) Assignee: Sanofi-Aventis Deutschland GmbH, Frankfurt am Main (DE)

( * ) Notice: Subject to any disclaimer, the term of this patent is extended or adjusted under 35 U.S.C. 154(b) by 1189 days.

(21) Appl. No.: 13/519,537

(22) PCT Filed: Jan. 24, 2011

(86) PCT No.: PCT/EP2011/050898
§ 371 (c)(1),
(2), (4) Date: Oct. 12, 2012

(87) PCT Pub. No.: WO2011/089246
PCT Pub. Date: Jul. 28, 2011

(65) Prior Publication Data
US 2013/0030381 A1 Jan. 31, 2013

Related U.S. Application Data

(60) Provisional application No. 61/305,596, filed on Feb. 18, 2010.

(30) Foreign Application Priority Data

Jan. 25, 2010 (EP) ..................... 10151498

(51) Int. Cl.
*A61M 5/24* (2006.01)
*A61M 5/315* (2006.01)

(52) U.S. Cl.
CPC ........... *A61M 5/24* (2013.01); *A61M 5/31535* (2013.01); *A61M 5/31541* (2013.01);
(Continued)

(58) Field of Classification Search
CPC ............ A61M 5/24; A61M 2005/2485; A61M 2005/2488; A61M 5/31576; A61M 5/31583
See application file for complete search history.

(56) References Cited

U.S. PATENT DOCUMENTS 533,575 A 2/1895 Wilkens
5,226,895 A 7/1993 Harris
(Continued)

FOREIGN PATENT DOCUMENTS

EP 0937471 A2 8/1999
EP 0937476 A2 8/1999
(Continued)

OTHER PUBLICATIONS

Form PCT/IPEA/416, Notification of Transmittal of the International Preliminary Report on Patentability issued in International Application No. PCT/EP2011/050898 dated May 24, 2012.

*Primary Examiner* — Shefali Patel
(74) *Attorney, Agent, or Firm* — McCarter & English, LLP

(57) ABSTRACT

A drive assembly comprises a guide nut, a lock, and a fastener, the fastener being movable with respect to the lock into and out of a position, in which the fastener engages the lock with the guide nut.

12 Claims, 3 Drawing Sheets

(52) U.S. Cl.
CPC ..... *A61M 5/31543* (2013.01); *A61M 5/31551* (2013.01); *A61M 5/31585* (2013.01); *A61M 2005/2407* (2013.01); *A61M 2005/2488* (2013.01)

(56) References Cited

U.S. PATENT DOCUMENTS

| | | | |
|---|---|---|---|
| 5,279,586 A | 1/1994 | Balkwill | |
| 5,304,152 A | 4/1994 | Sams | |
| 5,320,609 A | 6/1994 | Haber et al. | |
| 5,383,865 A | 1/1995 | Michel | |
| 5,480,387 A | 1/1996 | Gabriel et al. | |
| 5,505,704 A | 4/1996 | Pawelka et al. | |
| 5,582,598 A | 12/1996 | Chanoch | |
| 5,626,566 A | 5/1997 | Petersen et al. | |
| 5,674,204 A | 10/1997 | Chanoch | |
| 5,688,251 A | 11/1997 | Chanoch | |
| 5,827,232 A | 10/1998 | Chanoch et al. | |
| 5,921,966 A | 7/1999 | Bendek et al. | |
| 5,961,495 A | 10/1999 | Walters et al. | |
| 6,004,297 A | 12/1999 | Steenfeldt-Jensen et al. | |
| 6,193,698 B1 | 2/2001 | Kirchhofer et al. | |
| 6,221,046 B1 | 4/2001 | Burroughs et al. | |
| 6,235,004 B1 | 5/2001 | Steenfeldt-Jensen et al. | |
| 6,248,095 B1 | 6/2001 | Giambattista et al. | |
| 6,899,698 B2 | 5/2005 | Sams | |
| 6,936,032 B1 | 8/2005 | Bush, Jr. et al. | |
| 7,241,278 B2 | 7/2007 | Moller | |
| 2002/0052578 A1 | 5/2002 | Moller | |
| 2002/0120235 A1 | 8/2002 | Enggaard | |
| 2003/0050609 A1 | 3/2003 | Sams | |
| 2004/0059299 A1 | 3/2004 | Moller | |
| 2004/0210199 A1 | 10/2004 | Atterbury et al. | |
| 2004/0267207 A1 | 12/2004 | Veasey et al. | |
| 2005/0113765 A1 | 5/2005 | Veasey et al. | |
| 2006/0153693 A1 | 7/2006 | Fiechter et al. | |
| 2006/0184117 A1* | 8/2006 | Knight | A61M 5/24 604/135 |
| 2008/0234633 A1* | 9/2008 | Nielsen | A61M 5/24 604/208 |
| 2009/0275914 A1 | 11/2009 | Harms et al. | |
| 2009/0275916 A1 | 11/2009 | Harms et al. | |

FOREIGN PATENT DOCUMENTS

| | | |
|---|---|---|
| JP | 2008-526455 A | 7/2008 |
| JP | 5933454 B2 | 6/2016 |
| WO | 9938554 A1 | 8/1999 |
| WO | 0110484 A1 | 2/2001 |
| WO | 2006077466 A2 | 7/2006 |
| WO | 2009101005 A1 | 8/2009 |
| WO | 2009/132777 A1 | 11/2009 |

* cited by examiner

DRIVE ASSEMBLY FOR A DRUG DELIVERY DEVICE AND DRUG DELIVERY DEVICE

CROSS REFERENCE TO RELATED APPLICATIONS

The present application is a 35 U.S.C. 371 National Application of PCT/EP2011/050898 filed Jan. 24, 2011, which claims priority to European Patent Application No. 10151498.2 filed Jan. 25, 2010 and U.S. Provisional Patent Application No. 61/305,596 filed Feb. 18, 2010, the entire contents of which are incorporated entirely herein by reference.

FIELD

The present invention relates to a drive assembly with a reset mechanism for a drug delivery device and a drug delivery device incorporating such a drive assembly.

BACKGROUND

Portable drug delivery devices are used for the administration of a medicinal fluid or drug that is suitable for the self-administration by a patient. A drug injection device is especially useful in the shape of a pen, which can be handled easily and kept everywhere available. A type of drug delivery device is constructed to be refillable and reusable many times. A dose of a drug is delivered by means of a drive mechanism, which also allows to set the dose that is to be dispensed.

U.S. Pat. No. 5,827,232 discloses a medication delivery pen comprising a reusable pen body and a disposable cartridge assembly including a plunger. The cartridge assembly can be disassembled from the pen body after the medication therein has been exhausted, and the used cartridge assembly may be replaced.

It is an object of the present invention to disclose a new drive assembly for a drug delivery device and a new drug delivery device.

SUMMARY

This object is achieved by a drive assembly according to claim 1 and a drug delivery device according to claim 14. Further objects are achieved by variants and embodiments according to the dependent claims.

The drive assembly comprises a guide nut, a locking means, which can be moved radially with respect to an axis of the assembly in order to engage with the guide nut and to inhibit a rotation of the guide nut, and a fastener, which is provided to move the locking means radially with respect to the axis and to hold the locking means in a position in which the locking means is engaged with the guide nut.

The guide nut can be a single component or can be composed of two or more parts. It can especially be formed to guide the movement of a piston rod, by means of a screw thread, for example, and can have a threaded circular opening. The guide nut may be provided to engage with another component of the device by means of friction or by means of a structured surface, which may comprise teeth, grooves or spikes, for example, or similar structure elements.

The locking means can be any component that is suitable to engage with the guide nut in such a way as to inhibit a movement of the guide nut in some direction relatively to the locking means or to any device component that is stationary with respect to the locking means. The locking means can be designed according to the requirements of individual embodiments as described in the following. The locking means can comprise a pawl, a hook, a cantilever, or a leaf spring, for example. It can be resilient or resiliently mounted with respect to the guide nut and/or with respect to the fastener.

The fastener can be any component that is suitable to effect an engagement of the locking means with the guide nut. The fastener can be rigid or flexible, and can be formed of only one part or assembled of two or more parts. It can be formed to be a part of a component of the device or provided as a separate component. It can be designed to engage or couple with the locking means in any mechanical way that is suitable to change the relative position of the locking means with respect to the guide nut. The fastener can be moved or removed in such a way that an engagement of the locking means with the guide nut is released to allow a rotation of the guide nut; this feature can especially be provided for a reset operation.

An embodiment of the drive assembly may further comprise a body, in which the guide nut and the locking means are arranged. The body can be any housing or any component that forms part of a housing, for example. The body can also be some kind of an insert connected with an exterior housing. The body may be designed to enable the safe, correct, and/or easy handling of the assembly or of a device comprising the assembly. The body may be designed to engage with one or several further components, which may be a dosing mechanism, a cartridge, a plunger, a piston rod, or the like. The body can be intended to house, fix and/or guide the assembly or the device, and particularly to protect it from harmful liquids, dust or dirt. The body can be unitary or a multipart component of tubular or non-tubular shape. The body may house a cartridge, from which doses of a drug can be dispensed. The body can especially have the shape of an injection pen.

In an embodiment of the drive assembly, the guide nut may be rotatable with respect to a body. The locking means inhibits a rotation of the guide nut with respect to the body when the fastener engages the locking means with the guide nut.

An embodiment of the drive assembly may be provided to be used with a cartridge holder, which can be attached to and removed from a body. In such an embodiment, the fastener can be part of or fastened to the cartridge holder. The fastener engages the locking means with the guide nut when the cartridge holder is attached to the body. The fastener can particularly be provided by a protruding element of the cartridge holder.

A cartridge holder can be any unitary or multipart component that is intended to hold a cartridge containing a drug. The cartridge holder may be of cylindrical or tubular shape, for instance. It may be made of a transparent or opaque, a rigid or elastic material. The cartridge holder or an insert of the cartridge holder can be provided with engaging means like a screw thread or a bayonet joint, for instance. It may be provided with a nozzle and/or a means for attaching a needle or a needle assembly.

In an embodiment of the drive assembly, the locking means may be fastened to a body, and a cartridge holder may be attached to the body. A rotation of the cartridge holder with respect to the body moves the fastener into or out of the position, in which the fastener engages the locking means with the guide nut.

In further embodiments of the drive assembly, the guide nut may be a toothed wheel having notches or interspaces between the teeth, and the locking means may be a resilient or resiliently mounted pawl or cantilever comprising an edge or hook engaging the notches or interspaces.

Further embodiments comprise a piston rod and a screw thread, the screw thread coupling the guide nut and the piston rod and enabling a helical movement of the piston rod with respect to the guide nut, the helical movement comprising a rotation around an axis and a simultaneous shift along the axis. The guide nut, the locking means and the piston rod may be arranged in a body, and a web or interface of the body may be provided to inhibit a movement of the guide nut in the direction of the axis while permitting a rotation of the guide nut with respect to the body around the axis when the locking means is not engaged with the guide nut.

Further embodiments comprise a drive sleeve arranged within a body, the drive sleeve being coupled with a piston rod by means of a further screw thread. The screw thread and the further screw thread can have opposite senses of rotation.

Further embodiments comprise a clutch, by which the drive sleeve can be rotationally locked with respect to the body in a releasable manner. A shift of the drive sleeve with respect to the body along the axis may thus be converted into a helical movement of the piston rod with respect to the body when the drive sleeve is rotationally locked with respect to the body and the locking means is engaged with the guide nut.

The invention further relates to a drug delivery device comprising a drive assembly having a guide nut, a locking means, and a fastener, the fastener being movable with respect to the locking means into and out of a position, in which the fastener engages the locking means with the guide nut. The drug delivery device can have additional features according to the various embodiments of the drive assembly. Such a drug delivery device can particularly have the shape of an injection pen.

The drug delivery device can generally be a disposable or re-usable device designed to dispense a dose of a drug, which may be insulin, a growth hormone, a heparin, or an analogue and/or derivative thereof, for example. The device may be designed to be operated manually or electrically and may comprise a mechanism for setting a dose. The device may be further designed to monitor physiological properties like blood glucose levels, for example. Furthermore, said device may comprise a needle or may be needle-free.

BRIEF DESCRIPTION OF THE FIGURES

These and other features of the invention will become apparent from the following brief description of the drawings, detailed description and appended claims and drawings. Same elements are related with same reference numerals.

DETAILED DESCRIPTION

Figure 1:
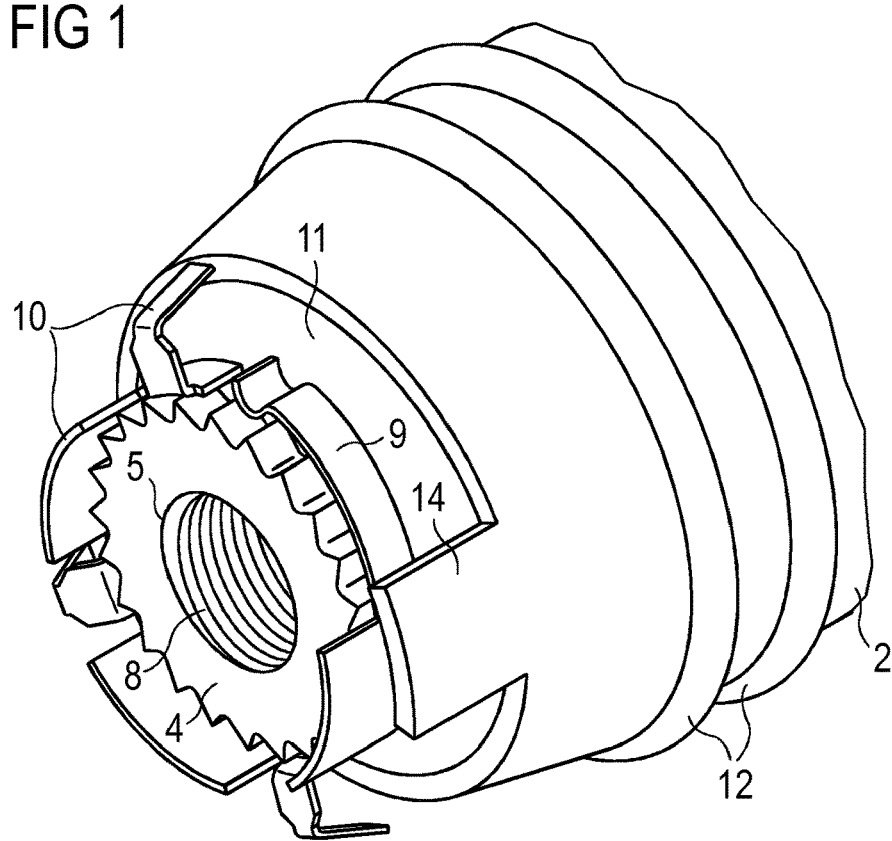
FIG. 1 shows a perspective view of a part of a drive assembly in a first operating position.

FIG. 1 shows a perspective view of a part of an embodiment of a drive assembly according to the invention. The guide nut 4 and the locking means 9 are arranged adjacent to one another and to a cartridge holder 2 carrying the fastener 14. FIG. 1 shows the situation in which the fastener 14 is out of the position, in which the fastener engages the locking means 9 with the guide nut 4.

The guide nut 4 can have a hole 5 in its centre and a screw thread 8 in the inner wall of the hole 5, which are provided to guide a piston rod or a leadscrew passing through the hole 5.

The guide nut 4 can also or alternatively have a hole 5 in its centre and features to provide a keyed engagement between a piston rod and the guide nut 4. The keyed engagement can be as such that a relative rotational movement between guide nut 4 and piston rod is prohibited. Such features can be protrusions and/or slots.

The cartridge holder 2 of this embodiment is tubular and provided with a cartridge compartment 11 and a screw thread 12. The opposite end of the cartridge holder 2, which does not make part of the drive assembly and is not shown in FIG. 1, can be provided with a nozzle or a needle for the administration of a drug from the cartridge. After a cartridge has been inserted in the cartridge compartment 11, the cartridge holder 2 is attached to a body of a drug delivery device comprising the drive assembly. The arrangement of the guide nut 4 and the locking means 9 may be mounted in the body by means of a mounting device 10, which can be formed by a suitably cut and bent metallic frame, for instance, as it is shown schematically in FIG. 1.

FIG. 1 shows a cartridge holder 2 as a typical example of a part of the device which carries the fastener 14. Instead of the cartridge holder 2 shown in FIG. 1, other embodiments may use an attachable and exchangeable reservoir or a removable part of a body or housing with an integrated ampoule. The screw thread 12 can be substituted with a bayonet coupling or a similar means for fastening. Irrespective of such details of the part carrying the fastener 14, this part and with it the fastener 14 are moved relatively to the arrangement of the guide nut 4 and the locking means 9 when the user changes an empty reservoir or ampoule or inserts a new cartridge.

When the fastener 14 is located excentrically, the movement of the fastener 14 may be a rotation with respect to the locking means 9. This is the case if the fastener 14 is located at the rim of a part like the cartridge holder 2, which is attached by means of a screw thread 12 and has therefore to be rotated.

The movement of the fastener 14 with respect to the locking means 9 can also be combination of rotational and linear components or a purely linear relative movement.

Figure 2:
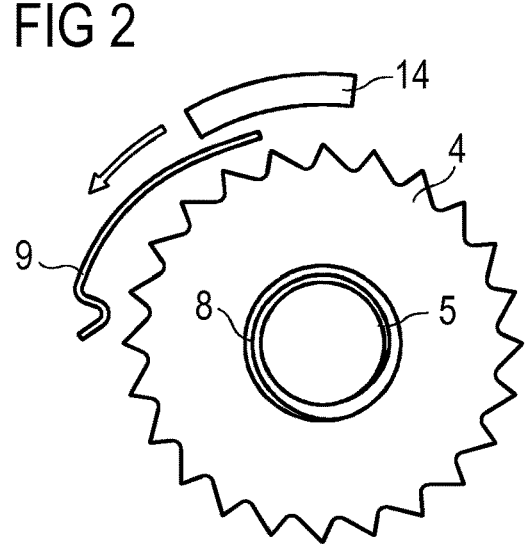
FIG. 2 shows a schematic frontal view of the part of the drive assembly according to FIG. 1.

FIG. 2 shows a schematic frontal view of the arrangement of the guide nut 4 and the locking means 9 when the fastener 14 is out of the position, in which the fastener engages the locking means 9 with the guide nut 4. The locking means 9 is a resilient element in this embodiment, and may especially be a leaf spring or a metal strip. It is mounted in the way of a pawl or cantilever with one end fastened to the mounting device 10 or to a body and the other end forming a hook. The locking means 9 is maintained at a distance from the guide nut 4 so that the locking means 9 and the guide nut 4 are not engaged and the guide nut 4 is free to rotate. The fastener 14 is moved in the direction of the arrow when the cartridge holder 2 is screwed to the body.

Figure 3:
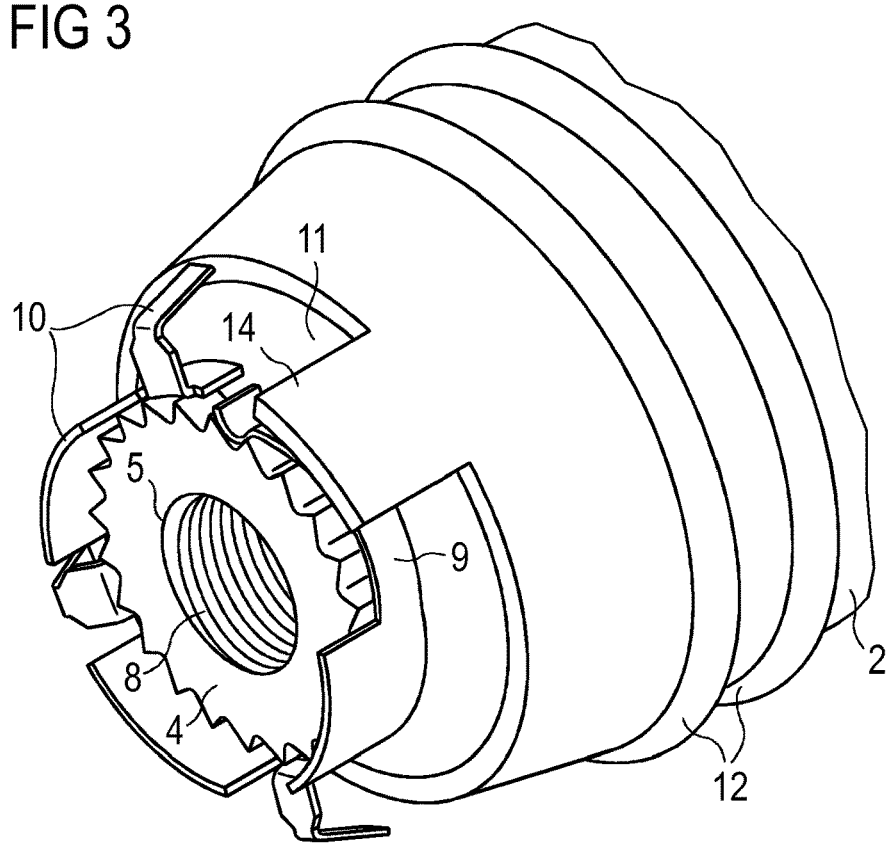
FIG. 3 shows a perspective view of the part of the drive assembly of FIG. 1 in a second operating position.

FIG. 3 shows a perspective view according to FIG. 1 after the attachment of the cartridge holder 2. The position of the fastener 14 with respect to the locking means 9 is now changed as compared to FIG. 1, owing to the rotation of the cartridge holder 2. The components and elements shown in FIG. 3 are the same as in FIG. 1 and bear the same reference numerals.

Figure 4:
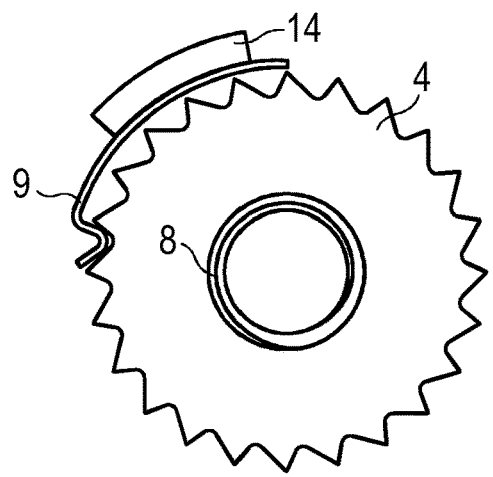
FIG. 4 shows a schematic frontal view of the part of the drive assembly according to FIG. 3.

FIG. 4 shows a schematic frontal view of the arrangement of the guide nut 4 and the locking means 9 when the fastener 14 is in the position, in which the fastener 14 engages the locking means 9 with the guide nut 4. A comparison with FIG. 2 shows that the fastener 14 has been moved on a circle that is concentric with the guide nut 4 and the fastener 14 has thus been caused to slide over the locking means 9, thus forcing the locking means 9 to engage with the structured outer surface of the guide nut 4. The guide nut 4 is a toothed wheel in this embodiment, the guide nut 4 and the locking means 9 forming a kind of ratchet, which inhibits a rotation of the guide nut 4 at least in one direction when the locking means 9 is engaged with the guide nut 4.

The movement of the fastener 14 may include a shift parallel to the central axis of the guide nut 4. Such a shift will especially occur if the cartridge holder 2 is attached by means of a screw thread 12 generating a helical movement. The function of the fastener 14 is not impaired by such a helical movement if the fastener 14 is dimensioned accordingly and is able to slide over the locking means 9 a certain distance also in the direction normal to the plane of the drawings of FIGS. 2 and 4.

FIGS. 1 to 4 represent only an example to show how the invention can be realized. The drive assembly can be modified in various ways without leaving the scope of the invention.

A drive assembly comprising a guide nut 4, a locking means 9 and a fastener 14 used in a drug delivery device will now be described in conjunction with FIG. 5 to explain further possible functions and operations of the drive assembly.

Figure 5:
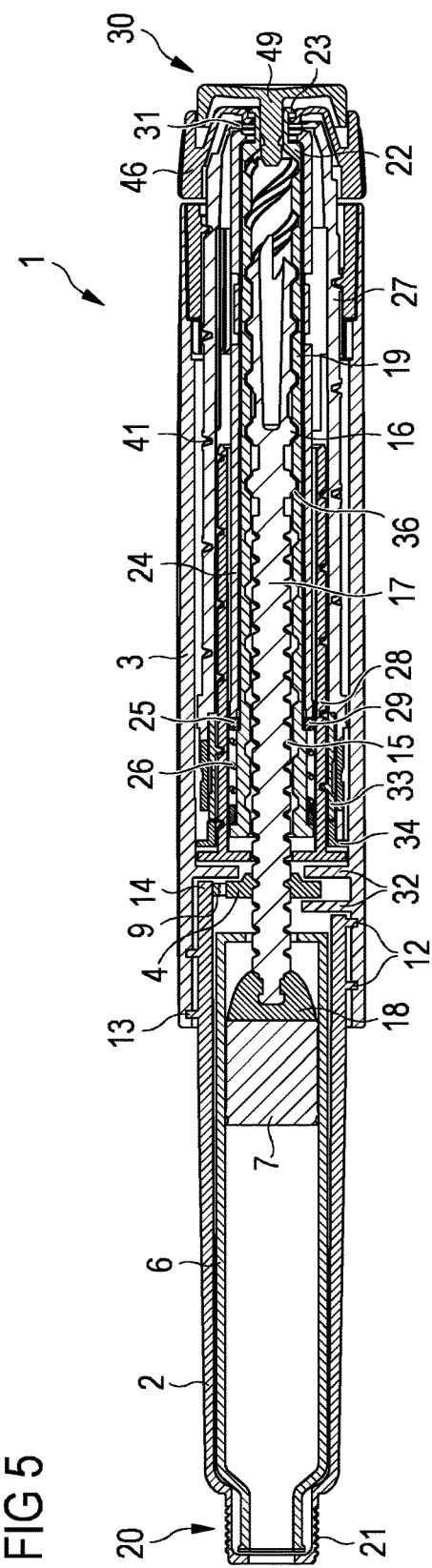
FIG. 5 shows a cross-section of an embodiment of the drug delivery device.

FIG. 5 shows a cross-section of an embodiment of the drug delivery device. The drug delivery device 1 comprises a body 3 with a distal end 20 and a proximal end 30 and a removable cartridge holder 2 at the distal end 20. The body 3 forms an exterior housing of the drug delivery device. The cartridge holder 2 is attached by a screw thread 12 mating a screw thread 13 of the main part of the body 3. Other means of fastening the cartridge holder 2, like a bayonet joint, are not precluded. The cartridge holder 2 is provided for a cartridge 6 containing a drug. A piston 7 is arranged in the cartridge 6 to be used to expel the drug. The distal end 20 may be provided with a nozzle 21, which can comprise a screw thread for the application of a needle assembly.

The drug delivery device 1 comprises a dosing mechanism, which includes a piston rod 17. The piston rod 17 has a distal end, which is nearest to the distal end 20 of the body 3 and engages the piston 7 or a bearing 18 that is arranged between the piston 7 and the piston rod 17 to reduce damages that may be caused by friction. The piston rod 17 is movable in the distal direction, i.e. towards the distal end 20, by means of a drive device, the piston rod 17 pushing the piston 7 within the cartridge 6 in the distal direction to expel the drug from the cartridge 6 through the nozzle 21. A first screw thread 15 of the piston rod 17 is formed towards the distal end, and a second screw thread 16 of the piston rod 17 is formed nearer to the proximal end of the piston rod 17. The first screw thread 15 and the second screw thread 16 have opposite senses of rotation in this embodiment. One or both of these screw threads 15, 16 may comprise two or more single screw threads in helical alignment, forming a so-called multi-start thread, which is known per se from other mechanical devices.

The drive device comprises a drive sleeve 19, which forms a tube through which the piston rod 17 is moved. The drive sleeve 19 is generally cylindrical and provided with a bearing 22 carrying a radially extending flange 23 at the proximal end. The second screw thread 16 of the piston rod 17 is coupled with a corresponding screw thread on the inner wall of the drive sleeve 19 to guide a helical relative movement of the piston rod 17 with respect to the drive sleeve 19.

A generally cylindrical clutch 24 is disposed around the drive sleeve 19, and the clutch 24 is at least partially surrounded by an end stop 28. The clutch 24 is located adjacent to the proximal end of the drive sleeve 19. Saw teeth 29 are arranged in azimuthal sequence at the distal end of the clutch 24, and further saw teeth 31 are arranged in azimuthal sequence at the proximal end of the clutch 24. The clutch 24 is keyed to the drive sleeve 19 by splines preventing a rotation of the clutch 24 relatively to the drive sleeve 19. The clutch 24 is provided with a plurality of flexible arms that engage a plurality of splines on an interior surface of a dose dial sleeve 27.

A clutch plate 25 and a biasing means 26 are located between the distal end of the clutch 24 and a radially extending flange at the distal end of the drive sleeve 19. The biasing means 26 may be a helical spring, for instance. The clutch plate 25 is rotationally locked to the body 3. The proximal face of the clutch plate 25 is provided with saw teeth interacting with the saw teeth 29 at the distal end of the clutch 24 during the operation of dose setting.

The end stop 28 is disposed between the drive sleeve 19 and the dose dial sleeve 27. The end stop 28 is rotationally locked to the body 3 and is free to move axially with respect to the body 3. In this embodiment, the external surface of the end stop 28 is provided with a helical groove or thread, which is engaged with a threaded insert 33 of the dose dial sleeve 27. The insert 33 is retained within the dose dial sleeve 27 by means of an end cap 34, which is locked both rotationally and axially with respect to the dose dial sleeve 27. Splines of the end stop 28 may be provided to engage with the clutch plate 25, thus locking the clutch plate 25 rotationally with respect to the body 3.

The dose dial sleeve 27 is provided with an outer helical thread 41 guiding a helical movement of the dose dial sleeve 27 with respect to the body 3. A dose dial grip 46 is disposed at the proximal end of the dose dial sleeve 27 and is provided with a central opening. A button 49 is provided at the proximal end 30 of the drug delivery device 1. The button 49 extends through the central opening of the dose dial grip 46 and enters the bearing 22 of the drive sleeve 19.

The first screw thread 15 of the piston rod 17 is guided by the screw thread 8 on the inner wall of the hole 5 of the guide nut 4. The guide nut 4 is prevented from axial movement with respect to the body 3 by means of a web 32. The web 32 can be provided by interfaces or protruding elements formed by integral parts of the body 3 extending transversely to the axis of the piston rod 17 into the interior volume of the body 3. The web 32 can instead be formed by separate components that are fastened to the body 3. The form of the web 32 is only restricted by its function to secure the guide nut 4 against an axial shift with respect to the body 3. To this end, the web 32 comprises parts located on the distal side and on the proximal side of the guide nut 4, as can be seen from FIG. 5.

The locking means 9 can be mounted on the inner wall of the body 3 or to an insert that is stationary with respect to the body 3. FIG. 5 shows the fastener 14 as a protruding part of the cartridge holder 2. The fastener 14 extends in proximal direction between the locking means 9 and the body 3 and can thus be made to slide over the locking means 9 by a rotation of the cartridge holder 2, when the cartridge holder 2 is screwed to the body 3 by means of the screw threads 12, 13. When the cartridge holder 2 is attached, the guide nut 4 is rotationally locked to the body 3 by the engaged locking means 9. When the cartridge holder 2 is removed, the guide nut 4 is released and free to rotate relatively to the body 3.

When the guide nut 4 is rotationally locked to the body 3, the movement of the piston rod 17 is guided by the screw thread 8 of the guide nut 4 engaging the first screw thread 15 of the piston rod 17. The movement of the piston rod 17 is thus restricted to a helical movement relatively to the body 3. When the guide nut 4 is not rotationally locked to the body 3, the movement of the piston rod 17 is no longer restricted by the guide nut 4. As the guide nut 4 is still not able to move axially because of the web 32, an axial shift of the piston rod 17 with respect to the body 3 requires a corresponding helical movement with respect to the guide nut 4. This helical movement is easily generated, because the disengagement of the guide nut 4 from the locking means 9 enables the guide nut 4 to rotate freely and with low friction with respect to the body 3 in a way to permit the movement of the piston rod 17.

The operation of the described embodiment of the drug delivery device will be described in the following.

To set a dose to be delivered, a user rotates the dose dial grip 46, thereby rotating the dose dial sleeve 27. The clutch 24 is engaged with the dose dial sleeve 27 by means of the saw teeth 31 at the proximal end of the clutch 24. This engagement and the splined engagement of the clutch 24 and the drive sleeve 19 make the clutch 24 and the drive sleeve 19 rotate with the dose dial sleeve 27. The clutch plate 25 is pushed towards the clutch 24 by the biasing means 26 in order to keep the saw teeth 29 of the clutch 24 and the saw teeth of the clutch plate 25 in contact. The profile of the saw teeth enables the relative movement of the clutch 24 and the clutch plate 25, which is rotationally locked to the body 3, and this relative movement provides an audible and tactile feedback of the set operation. The setting of a unit or a specified subunit of a dose can thereby be indicated, if the saw teeth are dimensioned accordingly.

The larger the dose to be set, the farther the dose dial sleeve 27 is moved out of the body 3. The relative movement of the dose dial sleeve 27 with respect to the body 3 is helical, because the coupling is effected by means of a screw thread. The pitch of the outer helical thread 41 of the dose dial sleeve 27, the pitch of the second screw thread 16 of the piston rod 17, and the coupling between the dose dial sleeve 27 and the piston rod 17 are adapted to enable the helical movement of the dose dial sleeve 27 with respect to the body 3 while leaving the piston rod 17 stationary with respect to the body 3. The piston rod 17 is maintained at its position during the set operation, because the movement of the piston rod 17 is restricted by the engaged guide nut 4.

The end stop 28, which is coupled to the dose dial sleeve 27 but prevented from rotating with respect to the body 3, moves in the proximal direction when the dose dial sleeve 27 is rotated out of the body 3. When a dose is set equal to the remaining dispensable contents of the cartridge 6, the end stop 28 abuts a stop means 36 of the piston rod 17, which prevents the end stop 28 and simultaneously the dose dial sleeve 27 from moving further in the proximal direction, and the set operation is stopped.

If the set dose is too large, the set operation can be corrected by rotating the dose dial grip 46 in the opposite direction. The reverse rotation of the clutch 24 makes the saw teeth of the clutch 24 override the saw teeth of the clutch plate 25.

When the desired dose has been set, it can be dispensed by pressing the button 49 in the distal direction. This displaces the clutch 24 in the distal direction with respect to the dose dial sleeve 27, thereby decoupling the clutch 24 and simultaneously the drive sleeve 19 from the dose dial sleeve 27. The clutch 24 remains rotationally locked to the drive sleeve 19. The dose dial sleeve 27 is now free to move helically back in the distal direction without causing a rotational or helical movement of the drive sleeve. The displacement of the clutch 24 also moves the clutch plate 25 in the distal direction against the biasing means 26, until the clutch plate 25 abuts a shoulder on the drive sleeve 19. The clutch 24 and the clutch plate 25 are thereby engaged, so that a rotation of the clutch 24 relatively to the clutch plate 25 is prevented. A rotation of the clutch 24 and the drive sleeve 19 with respect to the body 3 is thus also inhibited, because the clutch plate 25 is rotationally locked to the body 3 by means of the end stop 28. The clutch plate 25, the clutch 24 and the drive sleeve 19 are moved together in the distal direction but do not rotate with respect to the body 3.

The movement of the drive sleeve 19 causes a helical movement of the piston rod 17 with respect to the body 3 by means of the second screw thread 16 engaging the inner screw thread of the drive sleeve 19. As the movement of the piston rod 17 is also guided by the first screw thread 15 engaging the inner screw thread 8 of the guide nut 4, and the guide nut 4 is presently engaged with the locking means 9 and thus rotationally locked to the body 3, the helical movement of piston rod 17 advances the piston rod 17 in the distal direction. The ratio of the pitches of the first screw thread 15 and the second screw thread 16 can be selected according to a desired proportion between the distance by which the drive sleeve 19 is shifted and the distance by which the piston rod 17 is shifted relatively to the body 3 during the dispense operation. The movement of the dose dial sleeve 27 in the distal direction causes the end stop 28 to move back to its initial position within the body 3.

When the cartridge 6 is empty, it may be substituted with a new one. To this purpose, the cartridge holder 2 is removed from the body 3, the empty cartridge 6 is taken out of the cartridge compartment 11, and a new cartridge is inserted. Before the cartridge holder 2 is attached to the body 3, the piston rod 17 is reset to a start position, which is appropriate in view of the location that is occupied by the piston 7 when the cartridge holder 2 is attached.

The piston rod 17 is reset in the proximal direction. The movement of the piston rod 17 is restricted by the first screw thread 15 and the second screw thread 16 engaging the guide nut 4 and the drive sleeve 19, respectively. When both the guide nut 4 and the drive sleeve 19 are stationary with respect to the body 3, a movement of the piston rod 17 relatively to the body 3 is not possible because the first screw thread 15 and the second screw thread 16 do not have the same pitch and sense of rotation. The reset of the piston rod 17 by an axial movement in the proximal direction is possible when the guide nut 4 is free to rotate relatively to the body 3, thus enabling a helical movement of the guide nut 4 with respect to the piston rod 17 irrespective of the position and movement of the piston rod 17 with respect to the body 3.

The reset operation is therefore made possible by a release of the guide nut 4. As the fastener 14 is removed together with the cartridge holder 2, the locking means 9 is disengaged from the guide nut 4, as long as the cartridge holder 2 is not attached to the body 3. When the piston rod 17 is shifted in the proximal direction, the guide nut 4 rotates according to the required helical movement of the guide nut 4 with respect to the piston rod 17. When the piston rod 17 is reset, the cartridge holder 2 is attached to the body 3. The fastener 14 engages the locking means 9 with the guide nut 4, so that the guide nut 4 is rotationally locked to the body 3. The drug delivery device is then ready for set and dispense operations as described above.

The reset of the piston rod 17 can be performed manually, while the cartridge holder 2 stays completely removed. The reset can be achieved by pushing the piston rod 17 towards the proximal end 30 or by holding the device with the proximal end 30 pointing down to have the gravitational force move the piston rod 17 to the reset position. Instead, the piston rod 17 can be pushed by the piston 7 to the reset position, when the cartridge holder 2 is being attached and approaches the proximal end 30.

If the cartridge holder 2 is provided with a screw thread 12, it approaches the proximal end 30 slowly and steadily with every turn of the cartridge holder 2 with respect to the body 3 in the course of the attachment. The helical movement of the cartridge holder 2 with respect to the body 3, generated by a screw thread, has the advantage of not building up a load on the piston 7, which might shift the piston 7 before the drug delivery device 1 is used. If the cartridge holder 2 is provided with a bayonet coupling and there is no screw thread to control the smooth attachment of the cartridge holder 2, the reset of the piston rod 17 can be supported by means preventing a premature shift of the piston 7 towards the distal end 20.

The fastener 14 is preferably designed to enter the interspace between the body 3 and the locking means 9 automatically during the operation of attaching the cartridge holder 2. The design of the cartridge holder 2, and of the fastener 14 in particular, is preferably adapted to secure a complete reset of the piston rod 17 before the fastener 14 comes into the position in which the fastener 14 engages the locking means 9 with the guide nut 4.

An embodiment of the drug delivery device was described in detail in conjunction with FIG. 5, in order to make the drive assembly completely clear. The details of this embodiment in their entirety do not represent the essential features of the invention and do not restrict the scope of the invention as claimed. Various modifications, alterations and substitutions of the drive assembly and the drug delivery device are within the scope of the invention.

The drug delivery device has many advantages, among them the enablement of an easy replacement of the cartridge and a particularly easy reset of the piston rod. The reset operation thus need not be affected by details of the drive mechanism concerning the operations of setting and dispensing. The piston rod can therefore be provided with various functions and realized in various different embodiments, all of them enabling the reset operation as described. The drive assembly according to the invention renders the reset operation independent of the other operations of the drive mechanism and the piston rod.

The invention claimed is:

1. A drive assembly for a drug delivery device, comprising:
    a guide nut, the guide nut being rotatable around an axis of the assembly,
    a locking means, the locking means being radially movable with respect to the axis in order to engage with the guide nut and to inhibit a rotation of the guide nut,
    a body in which the guide nut and the locking means are arranged,
    a piston rod,
    a cartridge holder that can be attached to and removed from the body, and
    a fastener, the fastener being part of or fastened to the cartridge holder and being provided to move the locking means radially with respect to the axis thereby engaging the locking means with the guide nut when the cartridge holder is attached to the body, and to hold the locking means in a position in which the locking means is engaged with the guide nut for drug delivery,
    wherein
    a screw thread coupling the guide nut and the piston rod enables a helical movement of the piston rod with respect to the guide nut, the helical movement comprising a rotation around the axis and a simultaneous shift along the axis,
    the locking means is a resilient element having a first end fastened to the body, the locking means extending in an azimuthal direction from the first end to a second, free end for engaging with the guide nut,
    the fastener is a longitudinally protruding part of the cartridge holder, and
    the fastener is moved on a circle that is concentric with the guide nut, and is thus made to slide over the locking means and engages the locking means with a structured outer surface of the guide nut by a rotation of the cartridge holder with respect to the body.

2. The drive assembly according to claim 1, wherein the guide nut is a toothed wheel having notches or interspaces between teeth, and the locking means comprises an edge or a hook engaging the notches or the interspaces.

3. The drive assembly according to claim 1, wherein the drive assembly is configured such that the locking means is not engaged with the guide nut during a reset operation when the cartridge holder is not attached to the body.

4. The drive assembly according to claim 1, further comprising: a web of the body inhibiting a movement of the guide nut in a direction of the axis while permitting a rotation of the guide nut around the axis when the locking means is not engaged with the guide nut.

5. The drive assembly according to claim 4, further comprising: a drive sleeve arranged within the body, the drive sleeve being coupled with the piston rod by means of a further screw thread.

6. The drive assembly according to claim 5, wherein the screw thread and the further screw thread have opposite senses of rotation.

7. The drive assembly according to claim 5, further comprising: a clutch, by which the drive sleeve can be rotationally locked with respect to the body in a releasable manner.

8. The drive assembly according to claim 7, wherein a shift of the drive sleeve with respect to the body along the axis is converted into a helical movement of the piston rod with respect to the body when the drive sleeve is rotationally locked with respect to the body and the locking means is engaged with the guide nut.

9. A drug delivery device comprising the drive assembly according to claim 1.

10. The drug delivery device according to claim 9, having a shape of an injection pen.

11. The drug delivery device according to claim 9, further comprising: a clutch, by which a drive sleeve can be rotationally locked with respect to the body in a releasable manner.

12. The drug delivery device according to claim 11, wherein the drive assembly is configured such that a shift of the drive sleeve with respect to the body along the axis is converted into a helical movement of the piston rod with respect to the body when the drive sleeve is rotationally locked with respect to the body and the locking means is engaged with the guide nut.

* * * * *

UNITED STATES PATENT AND TRADEMARK OFFICE
CERTIFICATE OF CORRECTION

PATENT NO. : 10,188,800 B2
APPLICATION NO. : 13/519537
DATED : January 29, 2019
INVENTOR(S) : Langley et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1218 days.

Signed and Sealed this
Twenty-seventh Day of August, 2019

Andrei Iancu
*Director of the United States Patent and Trademark Office*